US011733079B2

(12) United States Patent
Feng et al.

(10) Patent No.: US 11,733,079 B2
(45) Date of Patent: Aug. 22, 2023

(54) MEASURING THE FLOW RATE OF FLUIDS WITH DIELECTRIC CONTRAST ANALYSIS

(71) Applicant: ExxonMobil Technology and Engineering Company, Annandale, NJ (US)

(72) Inventors: Lang Feng, New York, NY (US); John J. Valenza, Pennington, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 0 days.

(21) Appl. No.: 17/307,086

(22) Filed: May 4, 2021

(65) Prior Publication Data

US 2021/0372838 A1  Dec. 2, 2021

Related U.S. Application Data

(60) Provisional application No. 63/029,748, filed on May 26, 2020.

(51) Int. Cl.
*G01F 1/74* (2006.01)
*G01F 1/661* (2022.01)
(Continued)

(52) U.S. Cl.
CPC ................ *G01F 1/74* (2013.01); *G01F 1/661* (2013.01); *G01F 1/88* (2013.01); *G01N 33/2823* (2013.01)

(58) Field of Classification Search
CPC ......... G01F 1/74; G01F 1/88; G01N 33/2823; E21B 41/0064; E21B 47/06; G01H 9/004; G01V 8/02; G01V 8/16
See application file for complete search history.

(56) References Cited

U.S. PATENT DOCUMENTS 5,101,163 A     3/1992   Agar
5,793,216 A *   8/1998   Constant ................ G01N 22/00
                                                                                 324/639

(Continued)

FOREIGN PATENT DOCUMENTS

| GB | 2430493 A | 3/2007 |
|---|---|---|
| WO | 2010/069307 A1 | 6/2010 |
| WO | 2020/018822 A1 | 1/2020 |

OTHER PUBLICATIONS

Hall et al, "Use of Venturi Meters In Multiphase Flow Measurement", Flow Measurement Centre National Engineering Laboratory Glasgow, UK, Hall A & Reader-Harris M, 1999.

(Continued)

*Primary Examiner* — John Fitzgerald
(74) *Attorney, Agent, or Firm* — Vorys, Sater, Seymour and Pease LLP; Iona N. Kaiser

(57) ABSTRACT

A method for estimating a flow rate of a material (e.g., a multiphase fluid) may include: flowing the material through one or more of a plurality of receptacles of a dielectric contrast analysis structure that includes: a bulk dielectric substance and the plurality of receptacles in the bulk dielectric substance; exposing the dielectric contrast analysis structure to incident electromagnetic radiation; detecting and analyzing a resultant electromagnetic radiation from the exposed dielectric contrast analysis structure to yield a phase fraction in the material and a phase distribution in the material; measuring a differential pressure across the dielectric contrast analysis structure; and estimating the flow rate of the material using the differential pressure, the phase fraction, and the phase distribution in the material.

12 Claims, 9 Drawing Sheets

(51) Int. Cl.
*G01F 1/88* (2006.01)
*G01N 33/28* (2006.01)

(56) References Cited

U.S. PATENT DOCUMENTS

| | | | |
|---|---|---|---|
| 6,327,914 | B1 | 12/2001 | Dutton |
| 6,849,852 | B2 * | 2/2005 | Williamson ....... G01N 21/3563 |
| | | | 250/341.6 |
| 7,679,374 | B2 | 3/2010 | Bromberg et al. |
| 7,908,930 | B2 * | 3/2011 | Xie ........................... G01F 1/44 |
| | | | 73/861.04 |
| 8,855,947 | B2 | 10/2014 | Sheila-Vadde et al. |
| 9,207,357 | B2 | 12/2015 | Steinhardt et al. |
| 9,207,400 | B2 | 12/2015 | Ouyang et al. |
| 9,645,130 | B2 * | 5/2017 | Xie ........................ G01N 22/00 |
| 10,890,542 | B2 * | 1/2021 | Edward ................... G01F 1/662 |
| 2007/0133746 | A1 * | 6/2007 | Ortiz Aleman ........... G01F 1/64 |
| | | | 378/59 |
| 2009/0079976 | A1 | 3/2009 | Cunningham et al. |
| 2011/0267074 | A1 | 11/2011 | Xie et al. |
| 2014/0252250 | A1 | 9/2014 | Botto et al. |
| 2019/0242733 | A1 | 8/2019 | Feng et al. |

OTHER PUBLICATIONS

Corneliussen et al., "Handbook of Multiphase Flow Metering", Norwegian Society for Oil and Gas Measurement (NFOGM), 2005, Revision 2.
Ismail et al., "Tomography For Multi-Phase Flow Measurement In The Oil Industry", Elsevier, Low Measurement and Instrumentation 16 (2005), pp. 145-155.
Hasan et al., "Experimental and Theoretical Study Of The Gas-Water Two Phase Flow Through A Conductance Multiphase Venturi Meter In Vertical Annular (wet gas) Flow", Elsevier, Nuclear Engineering and Design 241 (2011), pp. 1998-2005.
Viana et al., "Challenges of Multiphase Flow Metering In Heavy Oil Applications", SPE Heavy Oil Conference held in Canada, Society of Petroleum Engineerings, Jun. 11-13, 2013, pp. 1-12.
Falcone et al., "Key Multiphase Flow Metering Techniques", Developments in Petroleum Science, Elsevier, 2009, vol. 54, pp. 47-190.
Elobeid et al., "Pressure Drop Measurements in Venturi Meters of Different Beta Ratios For Oil-Water Flow Experiments", Arabian Journal for Science and Engineering, 2018, 43 pp. 6355-6374.
Weinsten, "Multiphase Flow in Coriolis Mass Flow Meters-Error Sources and Best Practices", International North Sea Flow Measurement Workshop, Emerson Process Management—Micro Motion, Inc., Oct. 26-29, 2010.
Man et al., "Photonic Band Gap in Isotropic Hyperuniform Disordered Solids With Low Dielectric Contract", Optic Express, 2013, 21, pp. 19972-19981.
The International Search Report and Written Opinion of PCT/US2019/013746 dated May 7, 2019.
International Search Report and Written Opinion of the International Searching Authority dated Jul. 23, 2021.

* cited by examiner

MEASURING THE FLOW RATE OF FLUIDS WITH DIELECTRIC CONTRAST ANALYSIS

CROSS-REFERENCE TO RELATED APPLICATIONS

This application claims the benefit of U.S. Provisional Application No. 63/029,748 filed on 26 May 2020, the entire contents of which are incorporated herein by reference.

FIELD OF INVENTION

This disclosure relates generally to estimating the flow rate of fluids including multiphase fluids.

BACKGROUND OF THE INVENTION

This section is intended to introduce various aspects of the art, which may be associated with exemplary embodiments of the present disclosure. This discussion is believed to assist in providing a framework to facilitate a better understanding of particular aspects of the present disclosure. Accordingly, it should be understood that this section should be read in this light, and not necessarily as admissions of prior art.

During operations related to hydrocarbon prospecting, production, and/or refinement, material, such as production fluid produced from a reservoir via a wellbore, will be examined. A production "fluid" may, in fact, contain multiple substances in multiple physical states including gases, liquid, and/or solids. For example, production fluid may include liquid hydrocarbons, liquid water, natural gas, and various particulates, such as sand or wax. The production fluid will be examined to estimate quantities, such as the fraction of water, and/or the fraction of hydrocarbon in gas state (as opposed to liquid state). The flow of the production fluid may also be examined to estimate quantities, such as the flow rate of the bulk production fluid, and/or the flow rate of the water phase of the bulk production fluid.

Conventional flow meters for flow speed/rate measurement, such as Venturi meter, Coriolis meter and Positive Displacement meter, are generally accurate for single phase flow. When said flow meters are used for multiphase flow, extensive additional calibration and testing are needed, which is achieved by implementing said flow meters in conjunction with another, independent technology that measures the substance fraction and distribution. The technologies used for measuring substance fraction and distribution include Electrical Impedance Tomography ("EIT"), Electrical Capacitance Volume Tomography ("ECVT"), wire mesh sensor, microwave sensor, Nuclear Magnetic Resonance ("NMR"), and radiography and tomography with radioactive source (e.g., Gamma Ray tomography). Microwave-based flow meters have been used to examine materials related to hydrocarbon prospecting, production, and/or refinement. For example, microwave transmission is routinely used in multiphase flow measurement. Microwave-based flow meters may infer dielectric constant information by measuring attenuation and time delay of microwave signals between two or more antennas. This information only reflects effective composite properties through the use of effective medium theories. These microwave-based flow meters do not indicate flow morphology, or work well at high water fraction. Furthermore, they are typically unreliable in the presence of gas, which is typical in many production environments. Other conventional microwave-based technologies may place microwave antennas across a dielectric monolith to detect a shift in resonant frequency due to the deposition of a new phase, such as conductive soot. These methods only work at low soot concentration, and do not elucidate the distribution of soot in the monolith.

Other techniques for morphology measurement include gamma ray tomography. However, this technique can be costly and may be subject to substantial regulatory challenges associated with radioactive sources. Another technique for morphology measurement includes electrical impedance tomography ("EIT"). However, this technique involves exposed electrode arrays in contact with the multiphase flow. These arrays are susceptible to erosion and corrosion, which often necessitates recalibration, and in extreme cases replacement or repair.

In the field of optics, guiding and splitting electromagnetic waves with dielectric structures is practiced, often with dielectric structures having symmetry or other designs. However these dielectric structures are designed and produced with the goal of manipulating the electromagnetic waves. The material make-up of the dielectric structure is fixed, not being subject to examination.

More efficient equipment and techniques to evaluate the flow rate of multiphase fluids related to hydrocarbon management would be beneficial.

SUMMARY OF INVENTION

This disclosure relates generally to estimating the flow rate of fluids including multiphase fluids. More specifically, exemplary embodiments relate to equipment and methods for examining the flow rate of multiphase fluids with dielectric contrast analysis. Such fluids may be found in a variety of process industries like hydrocarbon management, water management, $CO_2$ sequestration, food processing, consumer products, pharmaceuticals, and healthcare.

A method of the present disclosure comprises: flowing a material through one or more of a plurality of receptacles of a dielectric contrast analysis structure that comprises: a bulk dielectric substance and the plurality of receptacles in the bulk dielectric substance; exposing the dielectric contrast analysis structure to incident electromagnetic radiation; detecting and analyzing a resultant electromagnetic radiation from the exposed dielectric contrast analysis structure to yield a phase fraction in the material and a phase distribution in the material; measuring a differential pressure across the dielectric contrast analysis structure; and estimating a flow rate of the material using the differential pressure, the phase fraction, and the phase distribution in the material.

A system of the present disclosure comprises: an electromagnetic radiation source; a dielectric contrast analysis structure comprising: a bulk dielectric substance and a plurality of receptacles in the bulk dielectric substance, wherein the plurality of receptacles are configured to allow a material to flow through the plurality of receptacles from a first side of the bulk dielectric substance to a second side of the dielectric substance; a first flow line connected to the first side of the bulk dielectric substance; a second flow line connected to the second side of the bulk dielectric substance; a flow path for the material, the flow path comprising, in order, the first flow line, the plurality of receptacles, and the second flow line; a flow path that form a flow path for a material to flow through the receptacles; a first pressure sensor coupled to the first flow line; a second pressure sensor coupled to the second flow line; and an electromagnetic radiation detector, wherein the dielectric contrast analysis structure is between the electromagnetic radiation source and the electromagnetic radiation detector.

BRIEF DESCRIPTION OF THE DRAWINGS

The following figures are included to illustrate certain aspects of the disclosure, and should not be viewed as exclusive configurations. The subject matter disclosed is capable of considerable modifications, alterations, combinations, and equivalents in form and function, as will occur to those skilled in the art and having the benefit of this disclosure.

DETAILED DESCRIPTION OF THE INVENTION

Figure 1B:
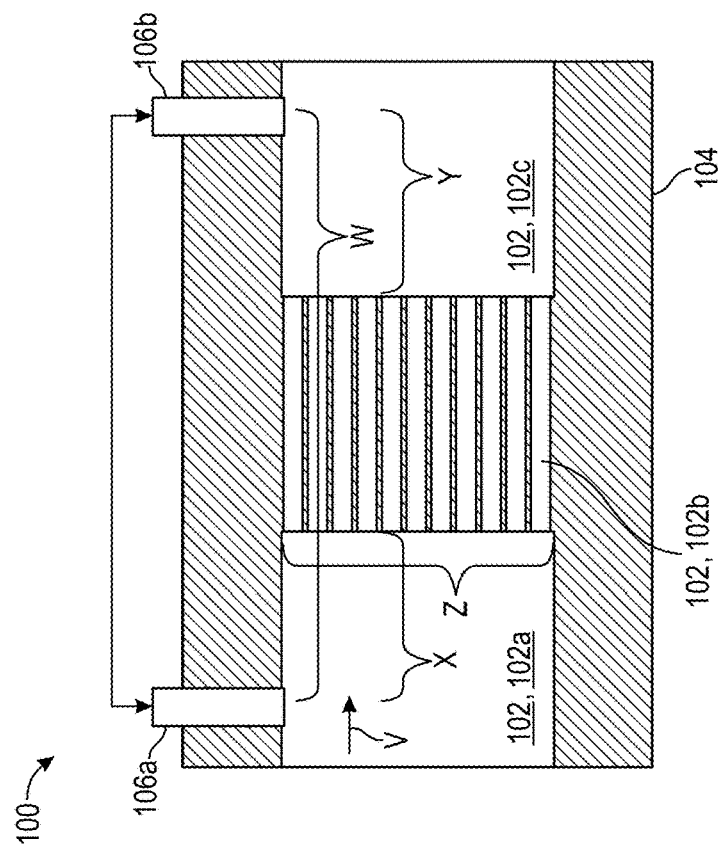
FIG. 1A and FIG. 1B illustrate cross-sectional views perpendicular to and parallel to a flow direction of a material through an exemplary integrated device, according to embodiments disclosed herein.

This disclosure relates generally to estimating the flow rate of fluids including multiphase fluids. More specifically, exemplary embodiments relate to equipment and methods for examining the flow rate of multiphase fluids with dielectric contrast analysis. Such fluids may be found in a variety of process industries like hydrocarbon management, water management, $CO_2$ sequestration, food processing, consumer products, pharmaceuticals, and healthcare.

As used herein, the term "state" generally refers to the physical state of a material, such as solid, liquid, or gas. "Phase" shall refer to the state, composition, and/or nature (identifiably distinct form) of a material. "Substance" shall refer to a mono-phasic material.

"Obtaining" data shall mean any method or combination of methods of acquiring, collecting, or accessing data, including, for example, directly measuring or sensing a physical property, simulating a physical property, receiving transmitted data, selecting data from a group of physical sensors, identifying data in a data record, and retrieving data from one or more data libraries. Data used in the methods and systems of the present disclosure may be simulated data, measured data, or a combination thereof.

The term "near-real time" refers to the time delay resulting from detecting, sensing, collecting, filtering, amplifying, modulating, processing, and/or transmitting relevant data or attributes from one point (e.g., an event detection/sensing location) to another (e.g., a data monitoring location). In some situations, a time delay from detection of a physical event to observance of the data representing the physical event is insignificant or imperceptible, such that near-real time approximates real time. Near-real time also refers to longer time delays that are still short enough to allow timely use of the data to monitor, control, adjust, or otherwise impact subsequent detections of such physical events.

As used herein, "hydrocarbon management" includes hydrocarbon extraction, hydrocarbon production, hydrocarbon exploration, hydrocarbon transportation, hydrocarbon storage, hydrocarbon refining, hydrocarbon characterization, and processing, identifying potential hydrocarbon resources, identifying well locations, determining well injection and/or extraction rates, identifying reservoir connectivity, identifying qualities and quantities of fluids in place in the reservoir, acquiring, disposing of, and/or abandoning hydrocarbon resources, reviewing prior hydrocarbon management decisions, and any other hydrocarbon-related acts or activities.

If there is any conflict in the usages of a word or term in this specification and one or more patent or other documents that may be incorporated herein by reference, the definitions that are consistent with this specification should be adopted for the purposes of understanding this disclosure.

This disclosure provides equipment and methods to measure/infer/estimate flow rate of a multiphase fluid using (a) differential pressure, (b) the phase fractions of the fluid (also referred to as phase fraction), and (c) the phase spatial distribution of the fluid (also referred to as phase distribution). The phase distribution describes, among other things, the flow regime (e.g., stratified, annular, churn, turbulent, dispersed, or slug).

Advantageously, the equipment and methods described herein are used as a single analysis device. More specifically, the phase fractions and phase spatial distribution are measured with dielectric contrast using electromagnetic waves and a dielectric contrast analysis structure. The differential pressure across the dielectric contrast analysis structure is also measured.

For example, some embodiments involve measuring the anisotropic transmission of electromagnetic energy to infer substance fraction and/or spatial distribution. Embodiments may be used to uncover oil/water/gas/sand phase fractions and flow morphologies in the multiphase flow (e.g., in a wellbore or pipeline or other line for application in other process industries). Combined with the differential pressure across the dielectric contrast analysis structure used in such measurements, the flow rate can be derived.

One of the many potential advantages of the embodiments of the present disclosure is that the measurement device may be incorporated into steel pipe for measuring the flow rate of multiphase fluid that may comprise oil/water/gas/sand phase fractions. Compared to current multiphase flow meters, embodiments of the present disclosure may be capable of operating at lower power. For example, measurements may be made utilizing antennas operating at between about 0.01 mW and about 10.0 mW, or between about 0.1 mW and about 1.5 mW, or approximately 1.0 mW. This technology may find applications in digital oil field/process technology. As used herein, the term "digital oil field" includes a broad range of technologies encompassing a wide variety of measurement tools and workflows. The overarching objective is to improve the profitability of hydrocarbon production operations over a wide range of time scales. Non-limiting examples of digital oil field technologies include autonomous control of operating facilities, data integration, decision support and automation, and production optimization. Production optimization, or near-real time production optimization, includes, but is not limited, to optimizing the production of a single well, or multiple wells up to and including the production of an entire field of wells. Optimization is achieved by utilizing production data from one or multiple wells, and/or an entire field. The well data include, but are not limited to, pressure, pressure drop, temperature, flow regime, flow rates, phase fractions, and the like, and any combination thereof. Embodiments of the present disclosure can thereby be useful in the prospecting, discovery, extraction, production, processing, transportation, and/or refinements of hydrocarbons from subsurface formations. Benefits may also include improvement in cost, ease of deployment, and accuracy in multiphase flow measurements. Beneficially, this may significantly increase opportunities for intelligent monitoring and/or near-real time production optimization in digital oilfield applications.

Some embodiments disclosed herein exploit the physics of photonic crystals. In particular, the photonic band structure may be identified and/or associated with the anisotropic interaction of electromagnetic waves with a spatial distribution of various phases of matter with dielectric contrast. The photonic band structure may be altered by substituting material, such as oil or water, into this spatial distribution of matter. Some embodiments may detect this phase substitution in order to measure phase fractions and/or spatial distribution of the material. Some embodiments may be able to achieve electromagnetic wave transmission in the frequency band where high water fraction, even complete water saturation, would normally preclude the propagation of electromagnetic energy. Some embodiments may be able to elucidate distribution or flow morphologies by exploiting simple symmetry principles.

The material to be examined may include one or more substances, solutions, mixtures, dispersions, bubbles, particulates, colloids, vesicles, and/or emulsions, of a single physical state or of multiple states. For example, the material may be a single substance (e.g., $H_2O$) of a single state or multiple states (e.g., ice, water, steam). As another example, the material may be a solution with the solute material of the same state(s) as the solvent material. As another example, the material may be a mixture made up of two or more different materials which are mixed but are not combined chemically. As another example, the material may be a dispersion in which particles of a first material are dispersed in a continuous phase of a different material (or phase). As another example, the material may be a colloid in which one material of microscopically dispersed insoluble particles is suspended throughout another material. As another example, the material may be a gas bubble in which one material of microscopically dispersed gas bubbles is suspended throughout another material. As another example, the material may be an emulsion mixing two or more liquids that are normally immiscible (unmixable or unblendable).

In some embodiments, the material to be examined may be production fluid. For example, the material may be a mixture of oil, gas, and water in fluid from an oil well and/or a reservoir. In such embodiments, examination of the material may include an evaluation of the water fraction flow rate of the production fluid, indicating the water proportion production rate and the hydrocarbon proportion production rate. Likewise, in such embodiments, examination of the material may include an evaluation of the gas-to-oil ratio of the production fluid, describing how many standard cubic feet of gas can be obtained for every stock tank barrel of oil. In some embodiments, the material to be examined may be a mixture of oil, sand, water, and/or clay in solid and/or fluid states from an oil well, a reservoir, and/or an oil-sand production facility. In such embodiments, examination of the material may include an evaluation of the material production rate or the production rate of individual components thereof.

Figure 1A:
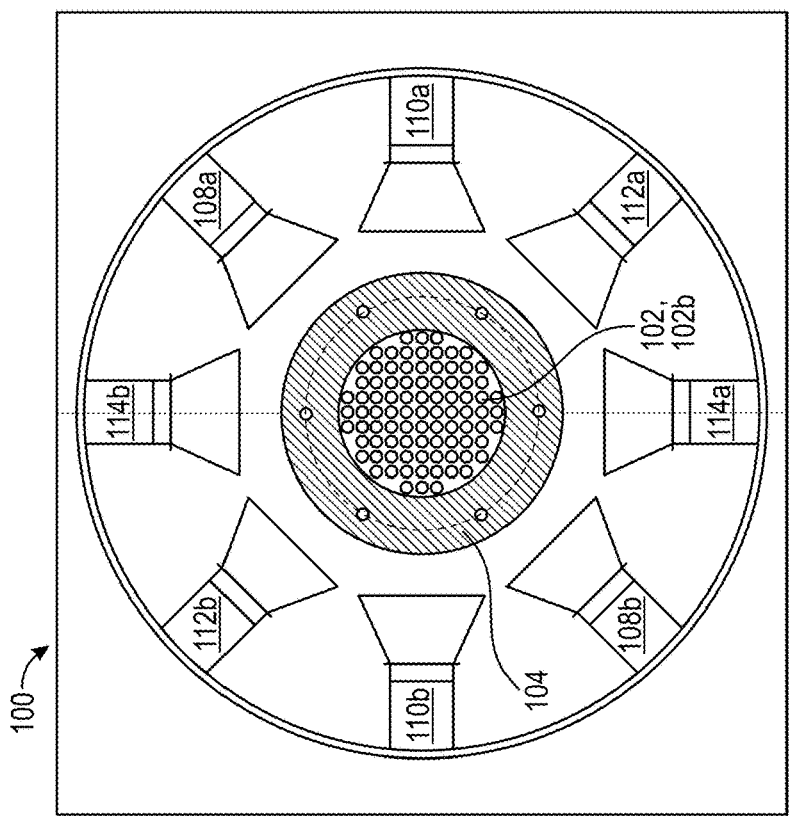

FIG. 1A and FIG. 1B illustrate cross-sectional views perpendicular to and parallel to a flow direction V of a material through an exemplary integrated device 100. The integrated device 100 includes a flow path 102 that comprises a first flow line 102a, a dielectric contrast analysis structure 102b, and a second flow line 102c. In the illustrated integrated device 100, the flow path 102 is, at least in part, formed by a housing 104, which may be a pipe, for example.

A first pressure sensor 106a is in communication with the material in the first flow line 102a so as to measure a pressure of the material therein, and a second pressure sensor 106b is in communication with the material in the second flow line 102c so as to measure a pressure of the material therein. The pressure difference between the first and second flow lines 102a, 102c is the differential pressure across the dielectric contrast analysis structure 102b. Examples of pressure sensors include, but are not limited to, hydrostatic pressure sensor, mechanical or aneroid pressure sensor, piezoresistive pressure sensor, piezoelectric pressure sensors, capacitive pressure sensor and magnetic pressure sensor, and the like, and any combination thereof.

The distance W between the first pressure sensor 106a to the second pressure sensor 106b along the flow path 102 may be about 100 cm or less (or about 5 cm to about 100 cm, or about 5 cm to about 25 cm, or about 25 cm to about 75 cm, or about 50 cm to about 100 cm).

While FIG. 1B illustrates the dielectric contrast analysis structure 102b as being placed evenly between the first pressure sensor 106a and the second pressure sensor 106b, the dielectric contrast analysis structure 102b can be placed anywhere between the two pressure sensors 106a and 106b. The distance X between the first pressure sensor 106a to the dielectric contrast analysis structure 102b along the flow path 102 may be about 99 cm or less (or about 1 cm to about 99 cm, or about 1 cm to about 25 cm, or about 25 cm to about 75 cm, or about 50 cm to about 99 cm). The distance Y between the second pressure sensor 106b to the dielectric contrast analysis structure 102b along the flow path 102 may be about 99 cm or less (or about 1 cm to about 99 cm, or about 1 cm to about 25 cm, or about 25 cm to about 75 cm, or about 50 cm to about 99 cm).

The size of the dielectric contrast analysis structure 102b is configured to match that of the interior of the flow path 102 so that the fluid flows therethrough. The diameter Z of the dielectric contrast analysis structure 102b (which is perpendicular to the direction of flow V) may be about 0.5 cm to about 200 cm (or about 2 cm to about 50 cm, or about 10 cm to about 30 cm, or about 15 cm to about 25 cm, or about 50 cm to about 100 cm).

For measuring the phase fractions and the phase spatial distribution of the material, the FIG. 1A example illustrates four pairs of transmitting and receiving antennas 108a/108b, 110a/110b, 112a/112b, 114a/114b arranged about the dielectric contrast analysis structure 102b. Embodiments of the dielectric contrast analysis structure 102b are described further herein and in U.S. Patent App. Pub. No. 2019/0242733, which is incorporated herein by reference.

More generally, the illustrated transmitting antennas 108a, 110a, 112a, and 114a are electromagnetic radiation sources, and the receiving antennas 108b, 110b, 112b, and 114b are electromagnetic radiation detectors. Examples of electromagnetic radiation sources include, but are not limited to, transmitting antennas, devices to generate a time varying electromagnetic field (for example a coil, a translating/rotating/oscillating permanent magnet such as Neodymium magnet, a electromagnet, a dipole antenna, a Yagi-Uta antenna, and a waveguide), and the like, and any combination thereof. Examples of electromagnetic radiation detectors include, but are not limited to, receiving antennas, devices to receive the electromagnetic radiation from at least one point or averaged over a sensing area, devices to convert the electromagnetic radiation signal to a digital or analogue signal that can be interpreted by a computer or observer (e.g., pickup coils), a dipole antenna, a Yagi-Uta antenna, superconducting RF SQUID detector, and the like, and any combination thereof. The transmitting/receiving antennas 108a/108b, 110a/110b, 112a/112b, 114a/114b may be, for example, radio frequency and/or microwave antennas, such as a 3115 Double-Ridged Guide Antenna available from ETS-Lindgren.

While the antennas in FIG. 1A are illustrated as four pairs of transmitting and receiving antennas, in other embodiments, one or more of these antennas (e.g., up to seven in FIG. 1A) could serve as the electromagnetic radiation source or the transmitting antenna(s), and the remaining one or more of these antennas could serve as the electromagnetic radiation receiver or the receiving antenna(s).

More generally, the integrated devices and related methods described herein may use one or more electromagnetic radiation sources and one or more electromagnetic radiation detectors. The cumulative number of electromagnetic radiation sources and electromagnetic radiation detectors may be two or more (or 2 to 20, or 4 to 15, or 6 to 10) with at least one being an electromagnetic radiation source and at least one being an electromagnetic radiation detector. For example, one electromagnetic radiation source may be used in combination with two or more electromagnetic radiation detectors. In another example, one electromagnetic radiation detector may be used in combination with two or more electromagnetic radiation sources. In yet another example, two or more electromagnetic radiation sources may be used in combination with two or more electromagnetic radiation detectors.

The configuration of the electromagnetic radiation source(s) and the electromagnetic radiation detector(s) may also be adjusted. In FIG. 1A, the electromagnetic radiation sources and the electromagnetic radiation detectors are paired and placed across from each other relative to the dielectric contrast analysis structure 102b. Alternatively, the electromagnetic radiation source(s) and the electromagnetic radiation detector(s) may be angularly offset, whether in pairs or not.

Additionally, in some configurations, the electromagnetic radiation source(s) and the electromagnetic radiation detector(s) could be disposed on an annular stage with a rotation actuator around a dielectric contrast analysis structure placed in the annulus. Rotation of the annular stage would cause relative rotation between the dielectric contrast analysis structure and the electromagnetic radiation source(s)/detector(s).

As illustrated in FIG. 1A, the transmitting antennas 108a, 110a, 112a, and 114a and receiving antennas 108b, 110b, 112b, and 114b are generally on opposite sides of dielectric contrast analysis structure 102b. Transmitting antennas 108a, 110a, 112a, and 114a are configured to expose the dielectric contrast analysis structure 102b to incident electromagnetic radiation. An electromagnetic radiation source, such as the transmitting antennas 108a, 110a, 112a, and 114a, may be configured to generate incident electromagnetic radiation having one or more frequencies between about 1 MHz and about 100 GHz (or between about 100 MHz and about 50 GHz, or between about 1 GHz and about 20 GHz, or approximately 10 GHz). In some embodiments, the incident electromagnetic radiation may include a frequency band of interest that is based on the length scales and/or dielectric properties of the dielectric contrast analysis structure 102b. In some embodiments, the incident electromagnetic radiation may be linearly polarized (e.g., transverse electric modes). An electromagnetic radiation detector, such as the receiving antennas 108b, 110b, 112b, and 114b, are configured to detect resultant electromagnetic radiation from the exposed dielectric contrast analysis structure 102b.

Figure 2:
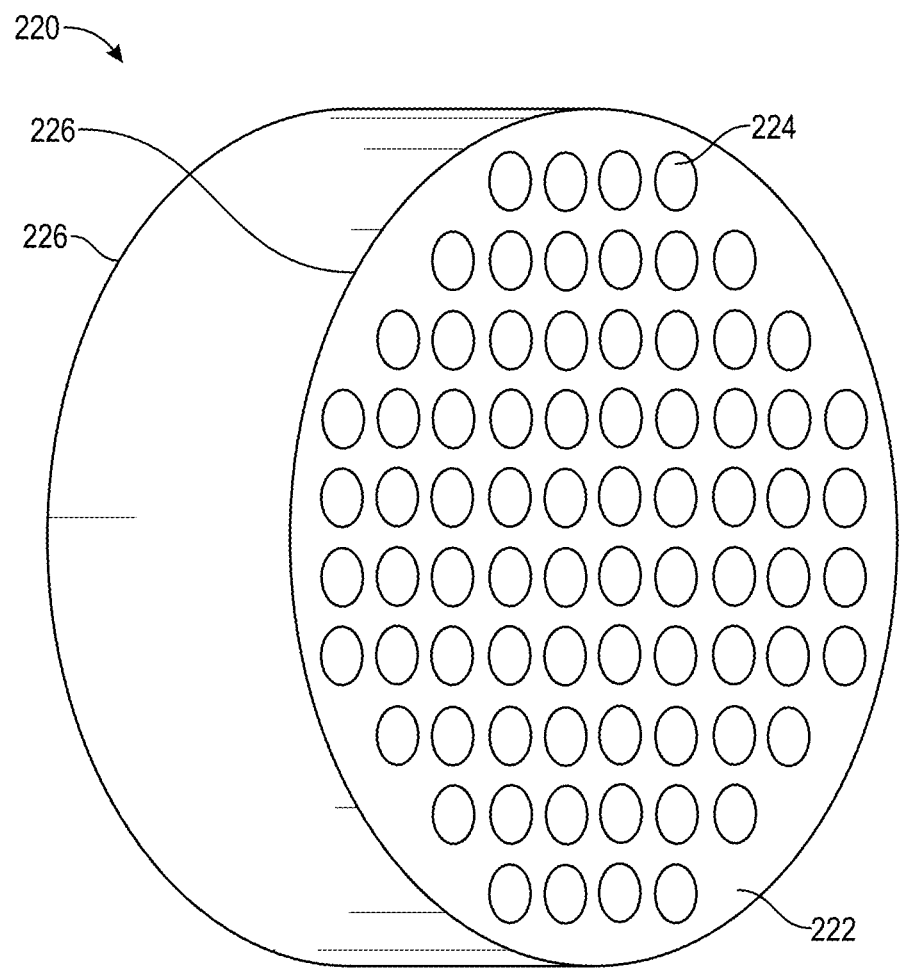
FIG. 2 illustrates an exemplary dielectric contrast analysis structure, according to embodiments disclosed herein.

FIG. 2 illustrates an exemplary dielectric contrast analysis structure 220, which is one of many configurations that may be implemented in the exemplary integrated device 100 of FIG. 1A. The dielectric contrast analysis structure 220 includes a bulk dielectric substance 222. As illustrated, the bulk dielectric substance 222 is generally cylindrical, but a variety of shapes (e.g., rectangular solid, conical) may be applicable to various manufacturing or operational conditions. The bulk dielectric substance 222 is made of dielectric materials. Examples of dielectric materials include, but are not limited to, polymers (e.g., polyethylene, polycarbonate, polyether ether ketone, an epoxy, a conducting polymer), ceramics (e.g., alumina, titania (titanium oxide), and ceramic ferrite), a composite material with a polymer matrix (e.g., nanoparticles dispersed in a polymer matrix and fibers dispersed in a polymer matrix), and the like, and any combination thereof.

In many embodiments, the dielectric contrast analysis structure 220 will have two ends 226 (e.g., cylinder ends). The ends 226 may or may not have the same surface area. Receptacles 224 are formed in the bulk dielectric substance 222. Generally, the receptacles 224 will extend between the two ends 226. In some embodiments, the receptacles 224 may be formed during manufacture of the bulk dielectric substance 222 (e.g., cast molded). In some embodiments, the dielectric contrast analysis structure 100 and the receptacles 224 may be formed with additive manufacturing or 3D printing processes including but not limited to selective laser melting, selective laser sintering, fused deposition modeling, and stereolithography. In some embodiments, the receptacles 224 may be subsequently cut, bored, milled, or otherwise formed into the bulk dielectric substance 222 by removing material therefrom. A variety of techniques for creating receptacles 224 in a bulk dielectric substance 222 may be applicable to various manufacturing or operational conditions. The receptacles 224 are intended to allow the material to be examined to flow therethrough. Generally, the receptacles 224 may have an opening in each end 226 of the dielectric contrast analysis structure 100.

In the illustrated embodiment, the receptacles 224 are regular cylindrical shapes, disposed parallel with one another, extending between ends 226, and arranged in a symmetric array (e.g., parallel rows, parallel columns, rows perpendicular to columns). Other shapes (e.g., hexagonal, square), alignments, planes of symmetry, and/or arrangements (e.g., honeycomb) of receptacles 224 may be applicable to various manufacturing or operational conditions. In addition, the arrangements of receptacles 224 may contain defects and/or imperfections that may be used to localize the EM energy, and/or correlate the measured transmission with a specific point in the structure. Without being limited by theory, it is believed that configurations with more planes of symmetry may provide more information about the phase distribution including the flow regime, for example.

The configuration of the dielectric contrast analysis structure 220 may be selected based on the expected properties of the material to be examined. For example, the dielectric constant (κ, also referred to as the relative dielectric permittivity, $\varepsilon_r$) of the material of the bulk dielectric substance 222 may be selected to provide high contrast with the expected dielectric constant of the material to be examined. In some embodiments, the dielectric constant of the bulk dielectric substance 222 may be selected to be between about 1.0 and about 100, or between about 1.5 and about 3.5, or between about 2 and about 3, or approximately 2.3. In some embodiments, the expected dielectric constant of the material to be examined may be between that of air (about 1) to that of water (about 80+20i in the microwave domain, where i is the imaginary square root of −1). As another example, the size, spatial distribution, and/or spatial density of the receptacles 224 in the bulk dielectric substance 222 may be selected to provide distinctive signals in the resultant electromagnetic radiation (discussed below). In some embodiments, the receptacles 224 may have a diameter of between about 1 mm and about 10 cm, or between about 10 mm and about 2 cm, or between about 100 mm and about 1.75 cm, or approximately 1.5 cm. In some embodiments, the spacing between adjacent receptacles 224, as measured from center to center, may be between about 0.1 cm and about 10.0 cm, or between about 1 cm and about 3 cm, or approximately 2 cm. Likewise, the size of the bulk dielectric substance 222 and/or number of receptacles 224 may be selected to provide distinctive signals in the resultant electromagnetic radiation. In some embodiments, the bulk dielectric substance 222 may have a diameter of between about 2 cm and about 100 cm, or 10 cm and about 30 cm, or between about 15 cm and about 25 cm, or approximately 21 cm. In some embodiments, the number of receptacles 224 in bulk dielectric substance 222 may be between about 10 and about 400, or between about 50 and about 100, or approximately 76.

As would be understood by one of ordinary skill in the art with the benefit of this disclosure, if the material to be examined in the receptacles has a non-zero conductivity σ, the full dielectric constant may be written as a complex number of the form $\varepsilon=\varepsilon_r+i\ \sigma/\omega$, where $\varepsilon_r$ may itself be a complex number as defined above and ω is the frequency. Conductivity of brine in typical hydrocarbon management environments can range anywhere from 1 mS/m to 10 S/m. It is convenient to define an index of refraction $n=\sqrt{(\varepsilon\mu)}$, where μ refers to the relative magnetic permeability. In almost all cases of relevance to this disclosure, μ=1, and the index of refraction can be simply written as the $n=\sqrt{\varepsilon}$. Since the dielectric constant may be a complex number, the index of refraction may also be a complex number with a real and imaginary part. Alternatively, it is also common to define an impedance $Z=\sqrt{(\mu/\varepsilon)}$. Depending on the context, this disclosure covers a measurement of any function of the dielectric constant of the examined medium, which can be determined, once the dielectric constant is obtained.

The dielectric contrast analysis structure 220 is configured to receive incident electromagnetic radiation and transmit resultant electromagnetic radiation, while the receptacles 224 are configured to contain and/or channel the flow of material to be examined. Therefore, the height (i.e., the distance between ends 226) of the dielectric contrast analysis structure 100 may be selected to better receive and transmit the electromagnetic radiation. In some embodiments, the height of dielectric contrast analysis structure 220 may be between about 2 cm and about 50 cm, or between about 10 cm and about 20 cm, or approximately 15 cm. In some embodiments, the dimensions of dielectric contrast analysis structure 220 may be configured to dispose the dielectric contrast analysis structure 220 within a wellbore, tubular within a wellbore, wellhead, surface pipeline, subterranean pipeline, ocean bottom pipeline, riser, or other equipment for handling production fluid.

Figure 3:
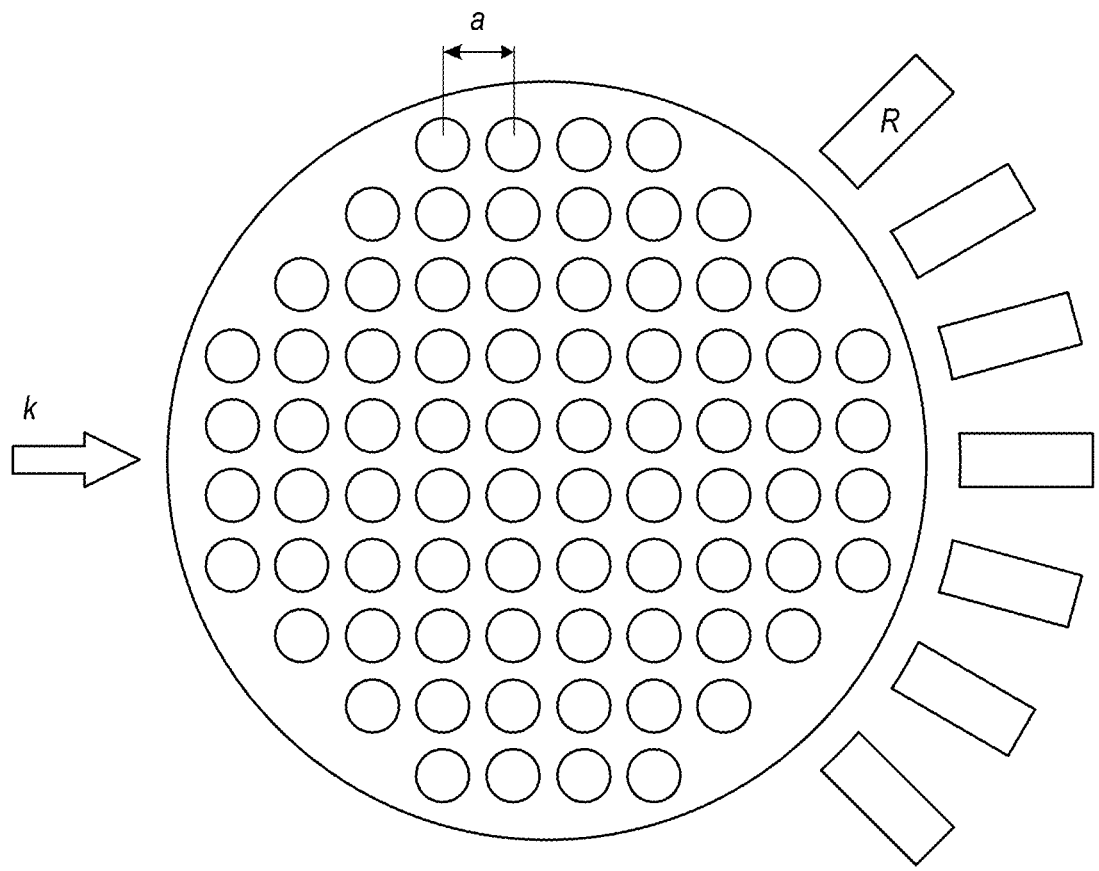
FIG. 3 illustrates a convention for referencing the results of incident electromagnetic radiation with a periodic dielectric contrast analysis structure, according to embodiments disclosed herein.

FIG. 3 illustrates a convention for referencing the results of incident electromagnetic radiation with a periodic dielectric contrast analysis structure, according to embodiments disclosed herein. Without being limited by theory, it is believed that after exposing the dielectric contrast analysis structure with periodicity a to an incident electromagnetic radiation k, the resultant electromagnetic radiation R as measured by one or more electromagnetic radiation detectors (e.g., around the perimeter of dielectric contrast analysis structure), can be described according to Bloch's theorem:

$$H_k(r) = e^{irk} u_k(r) \qquad (1)$$

$$u_k(r) = u_k(r+a) \qquad (2)$$

where:

$$\left\{\nabla \times \frac{1}{\varepsilon(r)} \nabla \times\right\} H(r) = \frac{\omega^2}{c^2} H(r) \qquad (3)$$

$$\varepsilon(r) = \varepsilon(r+a). \qquad (4)$$

Note that the magnetic field H has been expanded as a plane-wave in Equation 1. The symmetry of the lattice has been exploited in Equation 2. Note that Equation 3 is Maxwell's wave equation in frequency (ω) space, where ε is the permittivity (or dielectric constant) of the dielectric contrast analysis structure with the material to be examined, normalized to the permittivity of free space $\varepsilon_0=8.85\times10^{-12}$ F/m, and c is the speed of light. Equation 4 is thought to be valid when the material to be examined homogeneously fills all the receptacles.

The resultant electromagnetic radiation R may thus have frequency and/or angle dependency when exposed to incident electromagnetic radiation of wavelengths comparable to periodic feature sizing, for example when the ratio of wavelength and feature size is between about 0.01 and about 100 (or between about 0.1 and about 10, or between about 0.4 and about 2.5).

Figure 4:
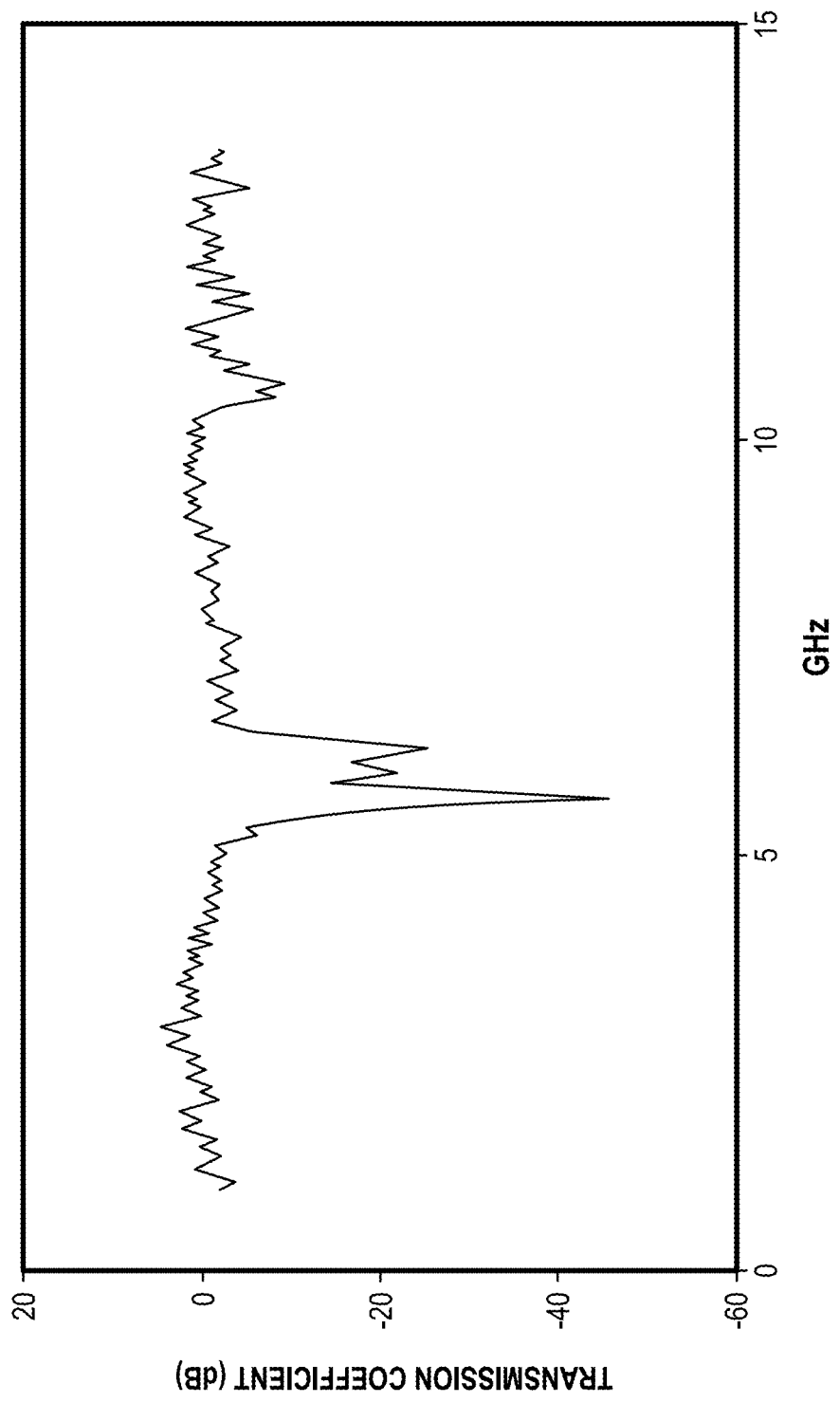
FIG. 4 illustrates a typical transmission coefficient measurement as a function of frequency of the incident electromagnetic radiation at a single angle/configuration.

Referring back to FIG. 2, when the dielectric contrast analysis structure 220 contains air (dielectric constant of about 1.0) in the receptacles 224, an anisotropic interaction may be observed between the incident electromagnetic radiation and the dielectric contrast analysis structure 220. The observed response may be related to a photonic band structure. A controller (e.g., a network analyzer) may be used to initiate transmission of electromagnetic radiation in the microwave band (about 1 GHz to about 40 GHz) from the transmitting antenna, for example at about 1 mW power. The receiving antenna may be used to measure the resultant electromagnetic radiation from the dielectric contrast analysis structure 220. FIG. 4 illustrates a typical transmission coefficient (in dB, defined as power ratio in decibels) measurement as a function of frequency of the incident electromagnetic radiation at a single angle/configuration (e.g., a receiving antenna directly opposite from a transmitting antenna) for the air-containing dielectric contrast analysis structure. The transmission coefficient of FIG. 4 represents a ratio of energies between resultant electromagnetic radiation and incident electromagnetic radiation, normalized by data acquired with a control structure which does not have any receptacles 224, while having the same diameter, height and dielectric constant of the dielectric contrast analysis structure 220.

U.S. Patent App. Pub. No. 2019/0242733, which is incorporated herein by reference, further describes methods to measure/infer the phase fractions of the fluid and the phase spatial distribution of the fluid.

Once the differential pressure across the dielectric contrast analysis structure, the phase fraction of a material flowing through the dielectric contrast analysis structure, and the phase distribution in the material are measured/inferred, the volumetric flow rate of the material through the receptacles of the dielectric contrast analysis structure is given by the following equation:

$$Q = A\sqrt{\Delta P} \quad (5)$$

where Q is the flow rate, A is a rate/pressure coefficient, and ΔP is the pressure drop across the dielectric contrast analysis structure.

For a conventional Venturi meter, in non-turbulent (e.g., at low-Reynolds number) single phase flow, A is a known function of fluid density, and several parameters associated with the shape and geometry of the Venturi meter such as the beta ratio, throat area, and the discharge factor. Therefore, for a single phase material flowing through the dielectric contrast analysis structure, one skilled in the art can readily derive A.

However, for a multi-phase flow system with transitions from non-turbulent to turbulent regimes, A is a complicated function of phase fractions, phase distributions (e.g., the flow regimes), density, and viscosity of the individual phases, and the geometry/shape of the structure the material is flowing through. While the density and viscosity of the individual phases may be determined through known testing methods, said values may, in the field, still vary over time (e.g., weeks). In addition, phase fractions and phase distributions of the multi-phase flow are typically highly dynamic. As a result, conventional flow rate measurements such as the Venturi meter cannot reliably relate the differential pressure measurement to a flow rate without one or more other devices to determine phase fractions and phase distributions. Other mass flow meters such as the Coriolis meter suffer complications that are intrinsic to the equipment design, such as the existence of entrained gas in the small U-shaped resonating tubes.

Advantageously, the dielectric contrast analysis structure measures phase fractions and distribution, which can be used to determine A. As described above, A is a function of phase fractions, phase distributions, density, and viscosity of the individual phases, and the geometry/shape of the structure the material is flowing through. Further, as illustrated in the examples below, A is statistically unique for the dielectric contrast analysis structure tested under the range of indicated phase distributions and phase fractions. Therefore, data gathered can be acquired over a wide range of known flow rates, known phase distributions (e.g., known flow regimes), known phase fractions, and known dielectric contrast analysis structures. Because these variables are known, A is known. Said data may be experimentally measured data, simulated data, or a combination thereof.

Then, said acquired data over a series of known variables can be used to build a data analytics model that may include one or more machine learning models. In some embodiments, the acquired data, again experimentally measured data, simulated data, or a combination thereof, can be used as machine learning datasets for training a machine learning model. The data analytics model is then implemented with the integrated device (e.g., integrated device 100 of FIG. 1A) to measure/derive flow rate of another material through the integrated device.

Figure 5:
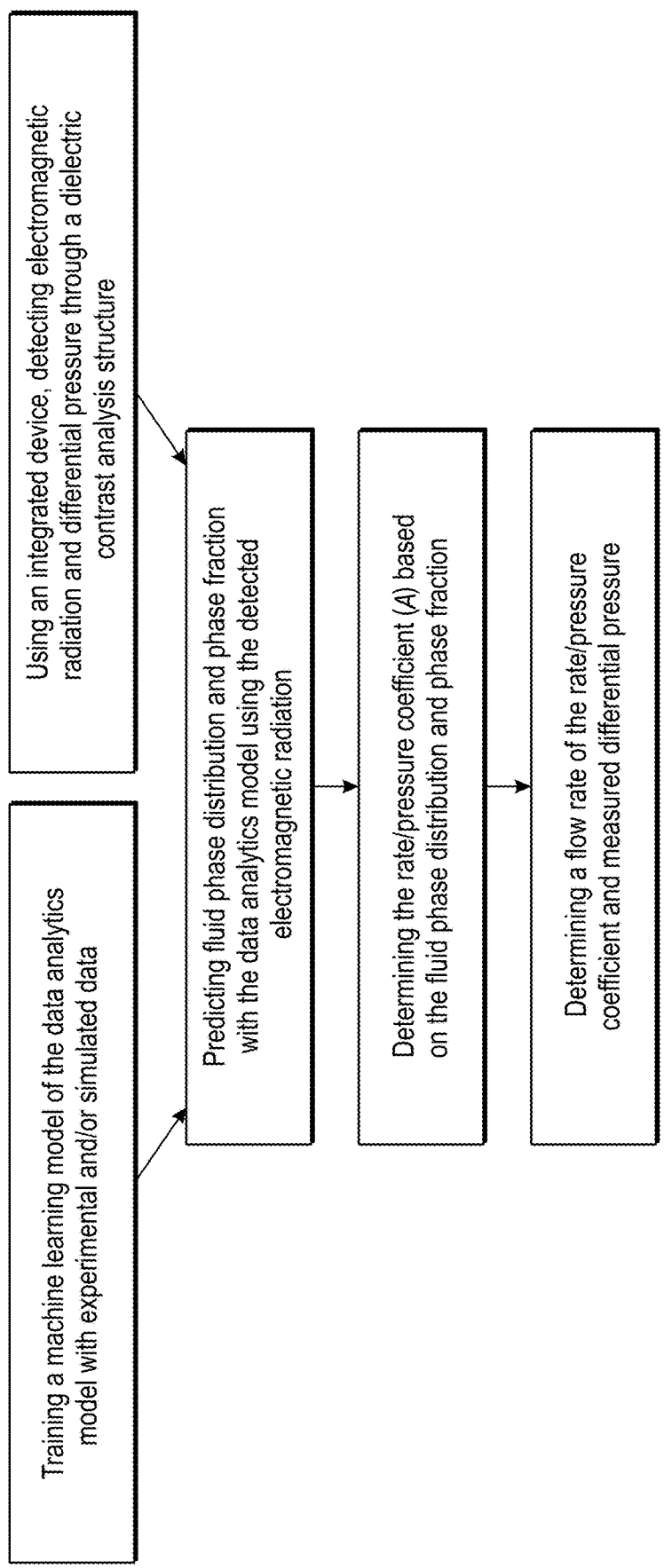
FIG. 5 is a flow chart that illustrates a nonlimiting example of a method of the present disclosure using a machine learning model in the data analytics model.

FIG. 5 is a flow chart that illustrates a nonlimiting example of a method of the present disclosure using a machine learning model in the data analytics model. In the illustrated method, a machine learning model is trained using experimental and/or simulated data. An integrated device described herein is used to measure the electromagnetic radiation and differential pressure through a dielectric contrast analysis structure.

The fluid phase distributions (e.g., flow regimes) and phase fractions are then predicted using the data analytics model using the detected electromagnetic radiation. Based on the fluid phase distribution and phase fraction, the rate/pressure coefficient (A) is then determined using the data analytics model. Finally, the flow rate is estimated based on A and the measured differential pressure across the dielectric contrast analysis structure.

As described above, the data analytics models described herein may include machine learning methods and algorithms that include, but are not limited to, polynomials, generalized linear model, elastic net, least absolute shrinkage and selection operator (Lasso), Ridge, boosting, extreme gradient boosting, support vector machine, neural networks, decision trees/random forest methods, kernal methods, multivariate adaptive regression (MARS) methods, polyMARS methods, reinforcement learning methods, Gaussian process models, and the like, and any ensemble thereof. Examples of neural networks include, but are not limited to, perception, feed forward, radial basis, deep feed forward, recurrent neural network, long-short term memory, gated recurrent unit, auto encoder, variational auto encoder, denoising auto encoder, sparse auto encoder, Markov chain, Hopfield network, Boltzmann machine, restricted Boltzmann machine, deep belief network, deep convolutional network, deconvolutional network, deep convolutional inverse graphics network, generative adversarial network, liquid state machine, extreme learning machine, echo state network, deep residual network, Kohonen network, neural turning machine, and the like. Examples of kernal methods include, but are not limited to, kernel perceptron, Gaussian processes, principal components analysis, canonical correlation analysis, ridge regression, spectral clustering, linear adaptive filters, and the like.

One or more machine-learning algorithms may be used to classify the datasets. For example, dimensionality reduction may be performed first to reduce the number of degrees of freedom in the data. For example, a thresholding procedure may be used to assign transmission coefficients into one or more bins. All the datasets may randomly split into two groups constrained to yielding the proportions 80:20 of non-overlapping training and test examples, respectively. One set of training input data could include transmission coefficient spectra/spectrum from one or more measurement orientations in an experimental polar intensity plot. By way of nonlimiting example, for a specific oil phase fraction and phase distribution having 500 datasets, one set of training input data may include the complete data from an experimental polar intensity plot from 400 randomly chosen datasets. Continuing nonlimiting example, if one set of training input data include a single transmission coefficient spectrum at a specific angle of an experimental polar intensity plot, there may be 1600 sets of training input data from 400 randomly chosen experiments each with 4 different angles. The training input data along with data labels (fraction of oil and phase distribution) are fed into one or more supervised machine learning classifiers to build a training model. The accuracy of the training model is then tested on the remaining 20% of the test data. The procedure is repeated for all training/test examples, and the resulting classifier algorithm is the mean of the classifiers.

By way of nonlimiting example, a method for determining flow rate may comprise: flowing a material through one or more of a plurality of receptacles of a dielectric contrast analysis structure that comprises: a bulk dielectric substance and the plurality of receptacles in the bulk dielectric substance; exposing the dielectric contrast analysis structure to incident electromagnetic radiation; detecting and analyzing a resultant electromagnetic radiation from the exposed dielectric contrast analysis structure to produce a phase fraction in the material and a phase distribution in the material; measuring a differential pressure across the dielectric contrast analysis structure; and measuring/deriving/estimating a flow rate of the material using the differential pressure, the phase fraction, and the phase distribution in the material (e.g., by applying the machine learning model described herein).

In another nonlimiting example, a system for determining flow rate may comprise: an electromagnetic radiation source; a dielectric contrast analysis structure comprising: a bulk dielectric substance and a plurality of receptacles in the bulk dielectric substance, wherein the plurality of receptacles are configured to allow a material to flow through the plurality of receptacles from a first side of the bulk dielectric substance to a second side of the dielectric substance; a first flow line connected to the first side of the bulk dielectric substance; a second flow line connected to the second side of the bulk dielectric substance; a flow path for the material, the flow path comprising, in order, the first flow line, the plurality of receptacles, and the second flow line; a flow path that form a flow path for a material to flow through the receptacles; a first pressure sensor coupled to the first flow line; a second pressure sensor coupled to the second flow line; and an electromagnetic radiation detector, wherein the dielectric contrast analysis structure is between the electromagnetic radiation source and the electromagnetic radiation detector.

In all practical applications, the aforementioned measurements and analyses must be used in conjunction with a data analysis system (e.g., a laptop and/or a high-speed computer) programmed in accordance with the disclosures herein. In some embodiment, the data analysis system is a high performance computer ("HPC"), as known to those skilled in the art. Such high performance computers typically involve clusters of nodes, each node having multiple CPUs and computer memory that allow parallel computation. The models may be visualized and edited using any interactive visualization programs and associated hardware, such as monitors and projectors. The architecture of the system may vary and may be composed of any number of suitable hardware structures capable of executing logical operations and displaying the output according to the present disclosure. Those of ordinary skill in the art are aware of suitable supercomputers available from Cray or IBM.

Figure 6:
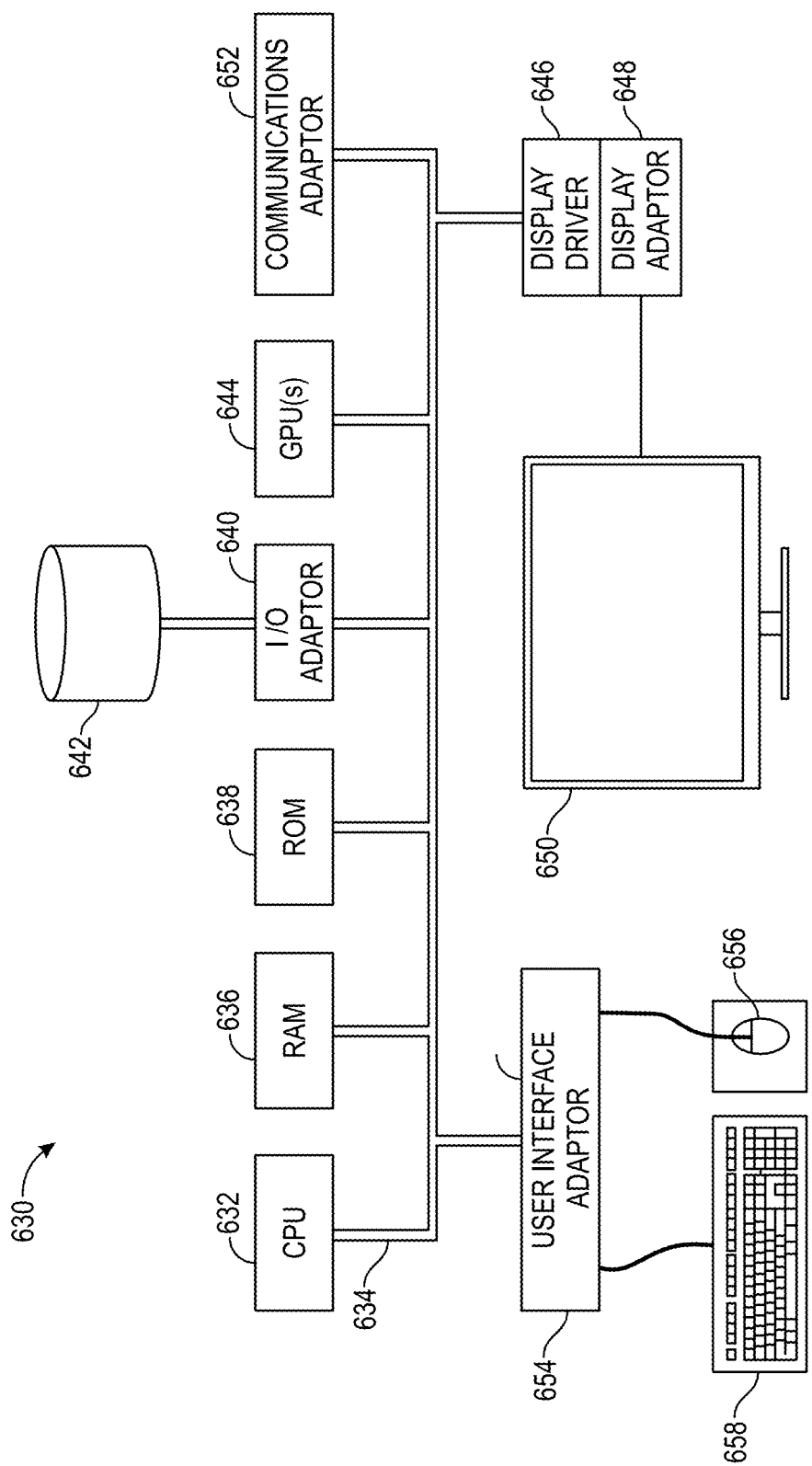
FIG. 6 illustrates a block diagram of a data analysis system, according to embodiments disclosed herein.

FIG. 6 illustrates a block diagram of a data analysis system 630 upon which the aforementioned plotting and/or analysis may be embodied. A central processing unit (CPU) 632 is coupled to system bus 634. The CPU 632 may be any general-purpose CPU, although other types of architectures of CPU 632 (or other components of exemplary system 630) may be used as long as CPU 632 (and other components of system 630) supports the operations as described herein. Those of ordinary skill in the art will appreciate that, while only a single CPU 632 is shown in FIG. 6, additional CPUs may be present. Moreover, the system 630 may comprise a networked, multi-processor or HPC computer system that may include a hybrid parallel CPU/GPU system and may be housed at a location that is far from that where the data is collected. The CPU 632 may execute the various logical instructions according to various teachings disclosed herein. For example, the CPU 632 may execute machine-level instructions for performing processing according to the operational flow described.

The data analysis system 630 may also include computer components such as non-transitory, computer-readable media. Examples of computer-readable media include a random access memory ("RAM") 636, which may be SRAM, DRAM, SDRAM, or the like. The system 630 may also include additional non-transitory, computer-readable media such as a read-only memory ("ROM") 638, which may be PROM, EPROM, EEPROM, or the like. RAM 636 and ROM 638 hold user and system data and programs, as is known in the art. The system 630 may also include an input/output (I/O) adapter 640, a communications adapter 652, a user interface adapter 654, and a display adapter 648.

The I/O adapter 640 may connect additional non-transitory, computer-readable media such as a storage device(s) (not illustrated), including, for example, a hard drive, a compact disc ("CD") drive, a floppy disk drive, a tape drive, and the like to data analysis system 630. The storage device(s) may be used when RAM 636 is insufficient for the memory requirements associated with storing data for operations of the present disclosure. The data storage of the system 630 may be used for storing information and/or other data used or generated as disclosed herein. For example, storage device(s) may be used to store configuration information or additional plug-ins in accordance with the present disclosure. Further, user interface adapter 654 couples user input devices, such as a keyboard 658, a pointing device 656, and/or output devices to the system 630. The display adapter 648 is driven by the GPU 644 and/or display driver 646 to control the display on a display device 650 to, for example, present information to the user regarding available plug-ins.

The I/O adapter 640 also connects to the integrated device 642 to receive signal inputs therefrom that are processed by the data analysis system 630.

The architecture of data analysis system 630 may be varied as desired. For example, any suitable processor-based device may be used, including without limitation personal computers, laptop computers, computer workstations, and multi-processor servers. Moreover, embodiments of the present disclosure may be implemented on application specific integrated circuits ("ASICs") or very large scale integrated ("VLSI") circuits. In fact, persons of ordinary skill in the art may use any number of suitable hardware structures capable of executing logical operations according to embodiments of the present disclosure. The term "processing circuit" encompasses a hardware processor (such as those found in the hardware devices noted above), ASICs, and VLSI circuits. Input data to the system 630 may include various plug-ins and library files. Input data may additionally include configuration information.

The integrated devices and/or data analysis systems described herein may be implemented in a variety of applications and configurations relative to materials (e.g., single phase fluids or multiphase fluid) for measuring/deriving the flow rate thereof.

By way of nonlimiting example, an integrated device and/or data analysis system described herein may be installed directly on a pipeline, production pipe, feedstock pipe, and the like. That is, a pipe section may be replaced by the integrated device so that all the material flowing through the primary line (e.g., pipeline, production pipe, or feedstock pipe) that contains the dielectric contrast analysis structure and related components of the integrated device. The flow rate through the primary stream may be measured using the integrated device and/or data analysis system.

In another nonlimiting example, an integrated device and/or data analysis system described herein may be installed along a side stream of a pipeline, production pipe, feedstock pipe, and the like. That is, a portion of the material flowing through the primary line (e.g., pipeline, production pipe, or feedstock pipe) may be diverted through a side stream that contains the dielectric contrast analysis structure and related components of the integrated device. The flow rate through the side stream may be measured using the integrated device and/or data analysis system. Then, the flow rate through the primary line may be derived therefrom, which may include further calculations to account for differences in geometry (e.g., cross-sectional diameter) between the side stream and the primary line.

While the methods and systems described herein for measuring/estimating fluid flow rates (e.g., for multiphase fluids) is predominantly discussed relative to hydrocarbon management, the methods and systems described herein are also applicable to other fluid processing applications like water management (e.g., water management in hydrocarbon production and waste water management), $CO_2$ sequestration, food processing, consumer product production, pharmaceutical production, and healthcare.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the incarnations of the present inventions. At the very least, and not as an attempt to limit the application of the doctrine of equivalents to the scope of the claim, each numerical parameter should at least be construed in light of the number of reported significant digits and by applying ordinary rounding techniques.

One or more illustrative incarnations incorporating one or more invention elements are presented herein. Not all features of a physical implementation are described or shown in this application for the sake of clarity. It is understood that in the development of a physical embodiment incorporating one or more elements of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

Example Embodiments

A first nonlimiting example embodiment of the present disclosure is a method comprising: flowing a material through one or more of a plurality of receptacles of a dielectric contrast analysis structure that comprises: a bulk dielectric substance and the plurality of receptacles in the bulk dielectric substance; exposing the dielectric contrast analysis structure to incident electromagnetic radiation; detecting and analyzing a resultant electromagnetic radiation from the exposed dielectric contrast analysis structure to yield a phase fraction in the material and a phase distribution in the material; measuring a differential pressure across the dielectric contrast analysis structure; and estimating a flow rate of the material using the differential pressure, the phase fraction, and the phase distribution in the material. The first nonlimiting example embodiment may include one or more of: Element 1: wherein the fluid is a multiphase fluid; Element 2: wherein the differential pressure is measured using a first pressure sensor and a second pressure sensor spaced about 200 cm or less from the first probe with the dielectric contrast analysis structure therebetween; Element 3: wherein the analyzing the resultant electromagnetic radiation comprises at least one of: (a) estimating at least one of a complex dielectric constant of the material, a complex permittivity of the material, a complex conductivity of the material, and a complex index of refraction of the material; (b) processing the detected resultant electromagnetic radiation to extract relevant low frequency information; and (c) averaging the detected resultant electromagnetic radiation over a range of orientations to improve signal-to-noise; Element 4: wherein the detecting the resultant electromagnetic radiation comprises: (a) measuring a first transmission coefficient of the resultant electromagnetic radiation through the dielectric contrast analysis structure along a first axis (orientation); and (b) measuring a second transmission coefficient of the resultant electromagnetic radiation through the dielectric contrast analysis structure along a second axis (orientation), different from the first axis; and wherein the analyzing the resultant electromagnetic radiation comprises: comparing the first transmission coefficient and the second transmission coefficient; Element 5: Element 4 and wherein the incident electromagnetic radiation comprises a plurality of frequencies; and wherein the comparing comprises plotting the first and second transmission coefficient measurements as functions of the plurality of frequencies and of a relative orientation of the first axis with respect to the second axis; Element 6: Element 4 and the method further comprising: measuring a plurality of transmission coefficients of the resultant electromagnetic radiation through the dielectric contrast analysis structure along a plurality of axes, each of the plurality of axes coplanar with the first axis and the second axis; Element 7: Element 6 and wherein the first axis, the second axis, and the plurality of axes are distributed symmetrically across a 360° arc; Element 8: Element 6 and wherein the incident electromagnetic radiation comprises a plurality of frequencies; wherein the comparing comprises creating plots of the first, second, and plurality of transmission coefficient measurements as functions of the plurality of frequencies and of relative orientations of the first axis, the second axis, and the plurality of axes; and wherein the analyzing further comprises statistically evaluating the plots; Element 9: Element 5 and wherein the analyzing further comprises: using data analytics methods and/or machine learning approaches to estimate the phase fraction and/or the phase distribution of the fluid based on the first transmission coefficient and the second transmission coefficient; Element 10: wherein the estimating the flow rate uses a data analytics model that comprises a machine learning model trained using measured data, simulated data, or a combination thereof; and Element 11: wherein the incident electromagnetic radiation comprises one or more frequencies between 1 megahertz and 100 gigahertz. Examples of combinations include, but are not limited to, Element 1 in combination with one or more of Elements 2-11; Element 2 in combination with one or more of Elements 3-11; Element 3 in combination with Element 4 (and optionally one or more of Elements 5-8) and optionally in further combination with one or more of Elements 9-11; Element 4 (and optionally one or more of Elements 5-8) in combination with one or more of Elements 9-11; and two or more of Elements 9-11 in combination.

A second nonlimiting example embodiment of the present disclosure is a system comprising: an electromagnetic radiation source; a dielectric contrast analysis structure comprising: a bulk dielectric substance and a plurality of receptacles in the bulk dielectric substance, wherein the plurality of receptacles are configured to allow a material to flow through the plurality of receptacles from a first side of the bulk dielectric substance to a second side of the dielectric substance; a first flow line connected to the first side of the bulk dielectric substance; a second flow line connected to the second side of the bulk dielectric substance; a flow path for the material, the flow path comprising, in order, the first flow line, the plurality of receptacles, and the second flow line; a flow path that form a flow path for a material to flow through the receptacles; a first pressure sensor coupled to the first flow line; a second pressure sensor coupled to the second flow line; and an electromagnetic radiation detector, wherein the dielectric contrast analysis structure is between the electromagnetic radiation source and the electromagnetic radiation detector. The second nonlimiting example embodiment may include one or more of: Element 12: wherein the electromagnetic radiation source comprises two or more electromagnetic radiation sources; Element 13: wherein the electromagnetic radiation detector comprises two or more electromagnetic radiation detectors; Element 14: wherein each of the plurality of receptacles is a generally elongated structure; the plurality of receptacles are generally parallel with one another; and wherein the plurality of receptacles are generally perpendicular to a path between the electromagnetic radiation source and the electromagnetic radiation detector; Element 15: wherein the second pressure sensor is spaced about 200 cm or less along the flow path from the first pressure sensor; Element 16: wherein at least one of the plurality of receptacles is generally cylindrical; Element 17: wherein the bulk dielectric substance comprises one or more materials having a relative dielectric permittivity within the range from about 1.0 to about 100; Element 18: wherein the bulk dielectric substance comprises a material selected from the group consisting of a polymer, a ceramic, a composite material with a polymer matrix, and any combination thereof; Element 19: wherein the electromagnetic radiation source and the electromagnetic radiation detector define a primary axis (orientation) therebetween; and wherein the electromagnetic radiation detector is capable of detecting resultant radiation from the dielectric contrast analysis structure along at least one axis offset from the primary axis; Element 20: wherein the electromagnetic radiation detector is capable of simultaneously detecting resultant radiation from the dielectric contrast analysis structure along a plurality of axes (orientations) coplanar to the primary axis; Element 21: the system further comprising: a spectral analyzer coupled to the electromagnetic radiation detector; Element 22: the system further comprising: a rotation actuator coupled to at least one of the electromagnetic radiation source, the electromagnetic radiation detector, and the dielectric contrast analysis structure, and capable of actuating relative rotation between the dielectric contrast analysis structure and the at least one of the electromagnetic radiation source and the electromagnetic radiation detector; and Element 23: the system further comprising: a controller coupled to the electromagnetic radiation source, the electromagnetic radiation detector, and the rotation actuator, and capable of correlating measurements of detected resultant radiation with at least one of a frequency of incident radiation from the electromagnetic radiation source and an orientation of the detected resultant radiation relative to the incident radiation. Examples of combinations include: Element 12 in combination with one or more of Elements 13-23; Element 13 in combination with one or more of Elements 14-23; Element 14 in combination with one or more of Elements 15-23; Element 15 in combination with one or more of Elements 16-23; Element 16 in combination with one or more of Elements 17-23; Element 17 in combination with one or more of Elements 18-23; Element 18 in combination with one or more of Elements 19-23; Element 19 in combination with one or more of Elements 20-23; and two or more of Elements 21-23 in combination.

To facilitate a better understanding of the embodiments of the present invention, the following examples of preferred or representative embodiments are given. In no way should the following examples be read to limit, or to define, the scope of the invention.

EXAMPLES

Example 1

This example uses a pilot scale field test using an integrated device similar to integrated device 100 of FIG. 1A to assess the accuracy of the measurement technology under dynamic conditions consisting of flowing a mixture of fluids through the dielectric contrast analysis structure. The mixture of fluids may include primarily liquid such as oil and water. In this example, the oil may be ISOPARV™ (a mixture comprising isoalkanes and cyclic alkanes, available from ExxonMobil). A dataset includes, but are not limited to, one or more transmission coefficient spectrum/spectra, the polar intensity plots, differential pressure measurement, flow rate measurement measured with one or more commercial flow meters, and sight-glass camera image. Datasets were acquired with this experimental set-up while the fraction of oil was increased in the liquid phase (0% to 64% oil in water/oil mixture with 4% step size). For 0% oil fraction (100% water fraction), 500 datasets were acquired. For any specific fraction of oil from 4% to 64%, 1500 datasets were acquired consisting of 500 data sets each measured under three independent flow regimes: stratified, churn, and dispersed.

Figure 7C:
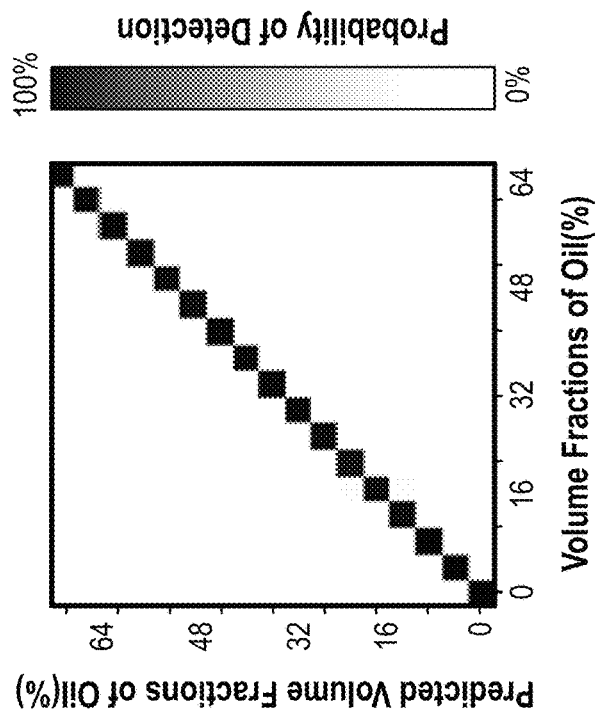
FIG. 7C illustrates a 2D probability histogram relative to the prediction accuracy of the models described herein.
Figure 7B:
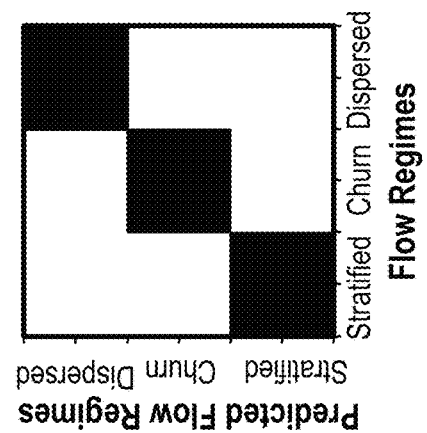
FIG. 7B illustrates a 2D probability histogram relative to the prediction accuracy of the models described herein.
Figure 7A:
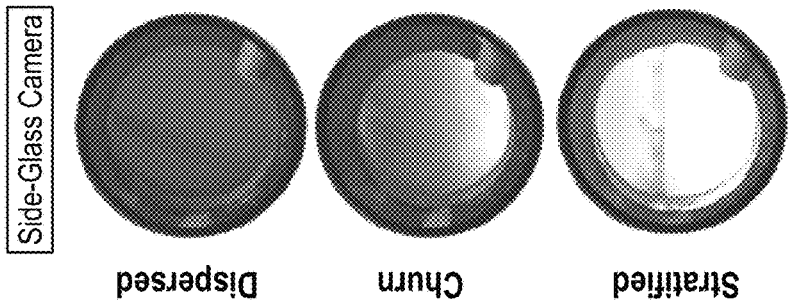
FIG. 7A illustrates exemplary photo images from a commercial sight glass camera to confirm the flow regime.

FIG. 7A illustrates exemplary photo images from a commercial sight glass camera to confirm the flow regime. From top to bottom, the three examples shown are dispersed flow regime with 44% oil fraction at about 250 GPM (gallons per minute), churn flow regime with 44% oil fraction at about 110 GPM, and stratified flow regime with 44% oil fraction at about 60 GPM.

FIG. 7B and FIG. 7C show results from a machine-learning analysis of the polar intensity plots from all datasets (24500 numbers of datasets) considering all oil fractions (0% to 64%) and flow regimes.

The 2D probability histogram in FIG. 7B shows the prediction accuracy by plotting the predicted flow regimes versus the true flow regimes verified by the direct site glass camera image (FIG. 7A). The greyscale colorbar represents the probability of detection, where black represents 100% and white represents 0%. FIG. 7B utilizes data from all datasets, and it shows an overall prediction accuracy of over 99%.

The 2D probability histogram in FIG. 7C shows the prediction accuracy by plotting the predicted phase fractions versus the true phase fractions. The greyscale colorbar represents the probability of detection, where black represents 100% and white represents 0%. FIG. 7C utilizes data from all datasets, and it shows an overall prediction accuracy of 96% and an R2score of 0.998. It is currently believed that even higher accuracy (or lower prediction error) can be obtained if we have a larger training data set (e.g., more data points for each oil fraction or smaller step size between oil fractions).

Example 2

This example utilizes the device in FIG. 1A as described in Example 1. The mixture of fluids in this example included gas (house nitrogen) and water. Datasets were acquired from experimental set-ups with increasing fractions of gas in the fluid phase (0% to 22.5% gas in gas/water mixture with 2.5% step size). For each specific fraction of gas, 1000 numbers of datasets were acquired.

Figure 8:
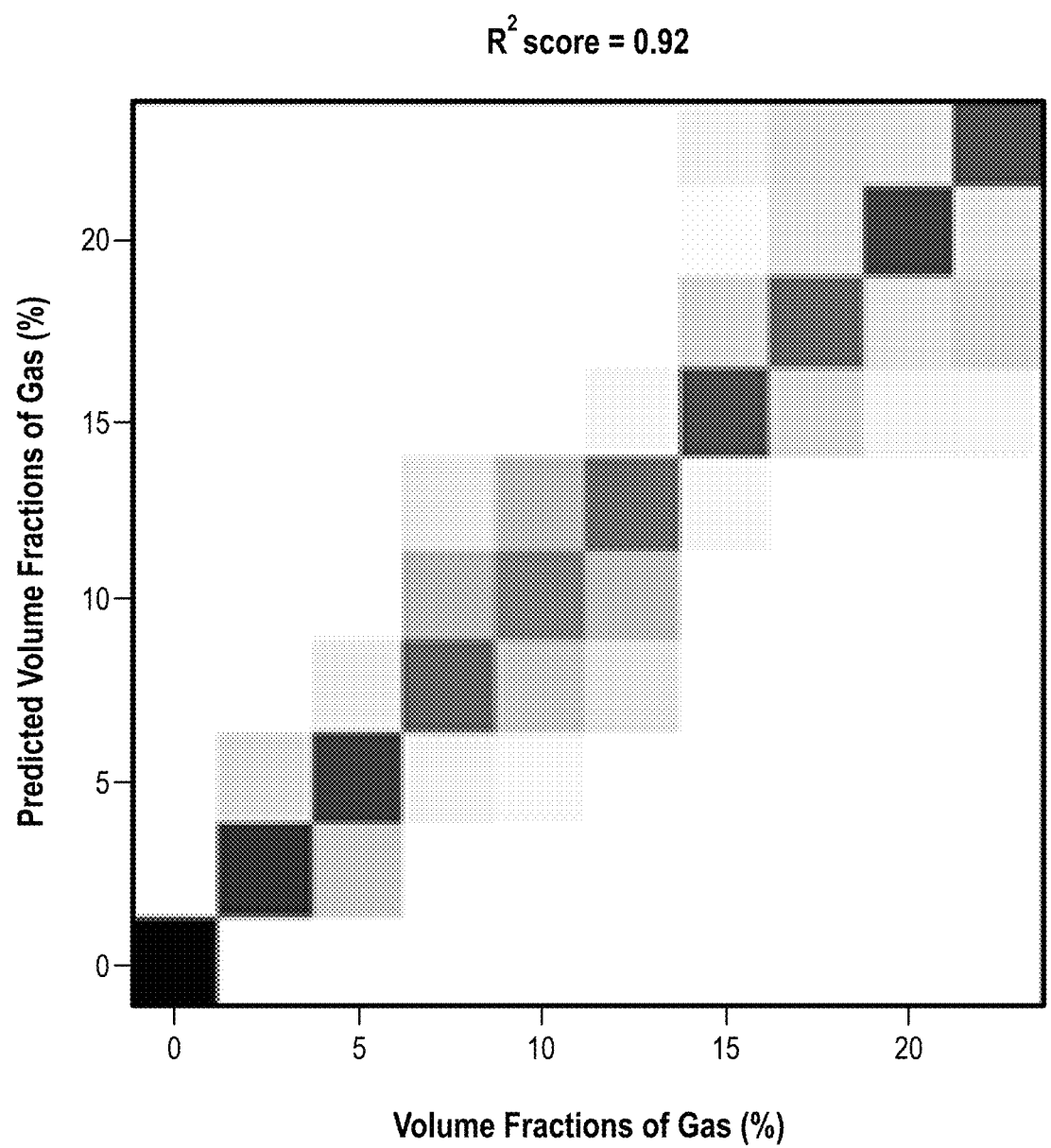
FIG. 8 illustrates a 2D probability histogram relative to the prediction accuracy of the models described herein.

FIG. 8 illustrates a machine-learning analysis of the polar intensity plots from all datasets (10000 numbers of datasets) across different fractions of gas from 0% to 22.5%. The 2D probability histogram in FIG. 8 shows the prediction accuracy by plotting the predicted phase fractions versus the true phase fractions. The greyscale color represents the probability of detection, with black represents 100% and white represents 0%. FIG. 8 utilizes data from all datasets, and it shows an R2score of 0.92. It is currently believed that even higher accuracy (or lower prediction error) can be obtained if we have a larger training data set (e.g., more data points per each gas fraction or smaller step size between gas fractions).

Example 3

Figure 9:
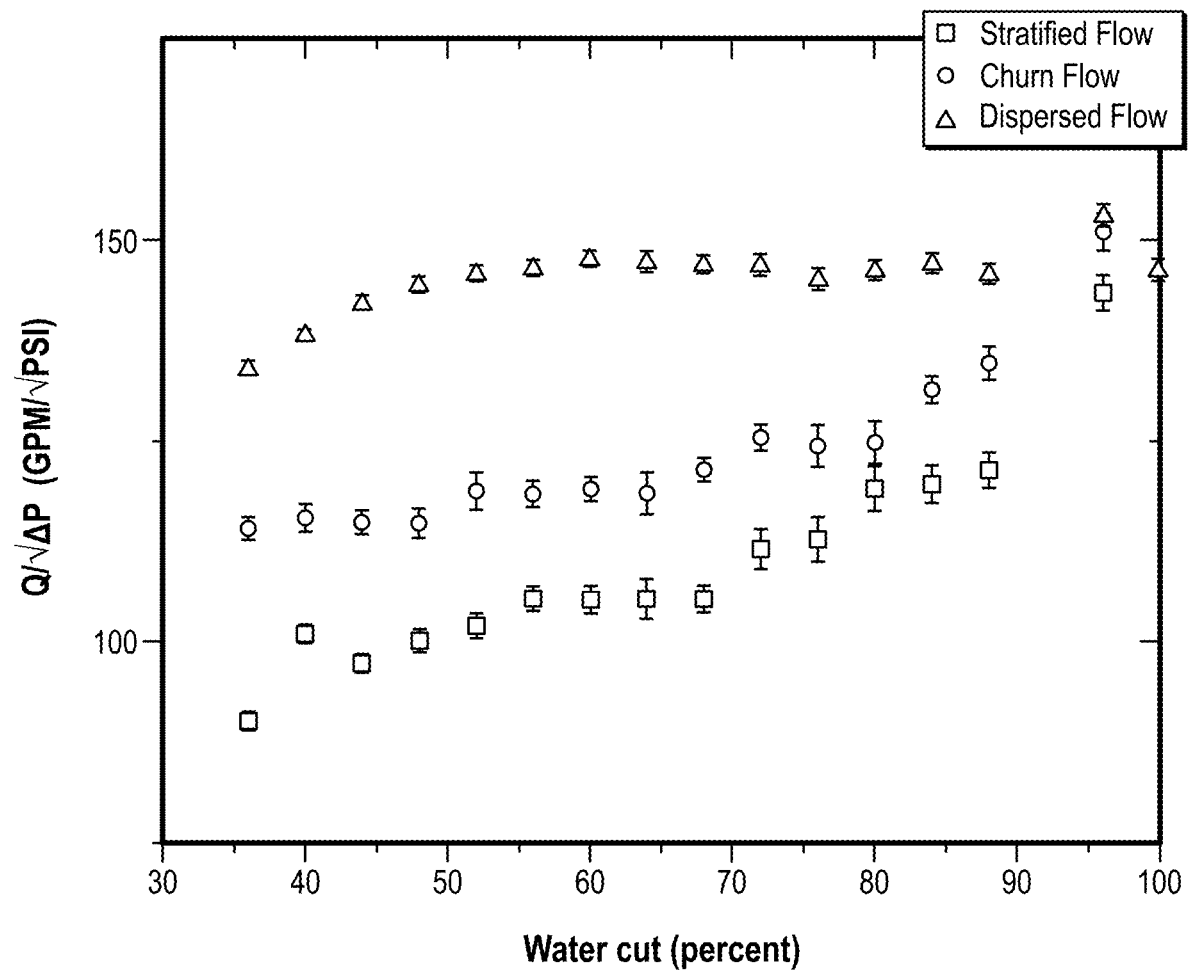
FIG. 9 is a plot of system specific constant A (Equation 5) as a function of water cut for the various flow regimes.

A plurality of samples with varying composition (water cut from 36% to 100% with a step size of 4%) and flow regime were passed through the dielectric contrast analysis structure of an integrated device as tested in Example 1. FIG. 9 is a plot of A as a function of water cut for the various flow regimes. FIG. 9 illustrates that Equation 5 above is statistically unique for the dielectric contrast analysis structure tested under the range of indicated flow regimes and phase fractions. For example, at 48% water cut with churn flow, the variation in A from the machine learning prediction for A has a small error bar on the order of 1%. This level of accuracy is expected for the entire range of parameters tested. With A, one can predict volumetric flow rate given a differential pressure measurement with an error bar of less than 2% overall.

Therefore, A can be directly acquired with the machine learning training datasets across a wide range of composition and across different flow regimes with the addition of the differential pressure measurement. It is important to note that while the data for inferring A shown in FIG. 9 is from an experiment at a flow loop, it is likely that similar data may be generated numerically using conventional computational fluid dynamic approaches.

Therefore, the present invention is well adapted to attain the ends and advantages mentioned as well as those that are inherent therein. The particular examples and configurations disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative examples disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. A method comprising:
   flowing a material through one or more of a plurality of receptacles of a dielectric contrast analysis structure that comprises: a bulk dielectric substance and the plurality of receptacles in the bulk dielectric substance;
   exposing the dielectric contrast analysis structure to incident electromagnetic radiation;
   detecting and analyzing a resultant electromagnetic radiation from the exposed dielectric contrast analysis structure to yield a phase fraction in the material and a phase distribution in the material;
   measuring a differential pressure across the dielectric contrast analysis structure; and
   estimating a flow rate of the material using the differential pressure, the phase fraction, and the phase distribution in the material.

2. A method according to claim 1, wherein the estimating the flow rate uses a data analytics model that comprises a machine learning model trained using measured data, simulated data, or a combination thereof.

3. The method of claim 1, wherein the incident electromagnetic radiation comprises one or more frequencies between 1 megahertz and 100 gigahertz.

4. A method according to claim 1, wherein the fluid is a multiphase fluid.

5. A method according to claim 1, wherein the differential pressure is measured using a first pressure sensor and a second pressure sensor spaced 200 cm or less from the first probe with the dielectric contrast analysis structure therebetween.

6. A method according to claim 1, wherein the analyzing the resultant electromagnetic radiation comprises at least one of:
   (a) estimating at least one of a complex dielectric constant of the material, a complex permittivity of the material, a complex conductivity of the material, and a complex index of refraction of the material;
   (b) processing the detected resultant electromagnetic radiation to extract relevant low frequency information; and
   (c) averaging the detected resultant electromagnetic radiation over a range of orientations to improve signal-to-noise.

7. A method according to claim 1, wherein: the detecting the resultant electromagnetic radiation comprises:
   (a) measuring a first transmission coefficient of the resultant electromagnetic radiation through the dielectric contrast analysis structure along a first axis (orientation); and
   (b) measuring a second transmission coefficient of the resultant electromagnetic radiation through the dielectric contrast analysis structure along a second axis (orientation), different from the first axis; and
   wherein the analyzing the resultant electromagnetic radiation comprises: comparing the first transmission coefficient and the second transmission coefficient.

8. A method according to claim 7 further comprising:
   measuring a plurality of transmission coefficients of the resultant electromagnetic radiation through the dielectric contrast analysis structure along a plurality of axes, each of the plurality of axes coplanar with the first axis and the second axis.

9. A method according to claim 8, wherein the first axis, the second axis, and the plurality of axes are distributed symmetrically across a 360° arc.

10. A method according to claim 8, wherein the incident electromagnetic radiation comprises a plurality of frequencies; wherein the comparing comprises creating plots of the first, second, and plurality of transmission coefficient measurements as functions of the plurality of frequencies and of relative orientations of the first axis, the second axis, and the plurality of axes; and wherein the analyzing further comprises statistically evaluating the plots.

11. A method according to claim 7, wherein the incident electromagnetic radiation comprises a plurality of frequencies; and wherein the comparing comprises plotting the first and second transmission coefficient measurements as functions of the plurality of frequencies and of a relative orientation of the first axis with respect to the second axis.

12. A method according to claim 11, wherein the analyzing further comprises: using data analytics methods and/or machine learning approaches to estimate the phase fraction and/or the phase distribution of the fluid based on the first transmission coefficient and the second transmission coefficient.

* * * * *